United States Patent
Duplessis et al.

(10) Patent No.: US 8,603,176 B2
(45) Date of Patent: Dec. 10, 2013

(54) ARTIFICIAL INTERVERTEBRAL SPACER

(75) Inventors: Stephan J. Duplessis, Calgary (CA); R. John Hurlbert, Calgary (CA); Lali Sekhon, Reno, NV (US)

(73) Assignee: Kinetic Spine Technologies Inc., Calgary, Alberta (CA)

( * ) Notice: Subject to any disclaimer, the term of this patent is extended or adjusted under 35 U.S.C. 154(b) by 74 days.

(21) Appl. No.: 12/909,700

(22) Filed: Oct. 21, 2010

(65) Prior Publication Data

US 2011/0093075 A1     Apr. 21, 2011

Related U.S. Application Data

(63) Continuation of application No. PCT/CA2009/000477, filed on Apr. 22, 2009.

(60) Provisional application No. 61/125,094, filed on Apr. 22, 2008.

(51) Int. Cl.
*A61F 2/44* (2006.01)

(52) U.S. Cl.
USPC .................. 623/17.16; 623/17.11; 623/17.15

(58) Field of Classification Search
USPC ........................................... 623/17.11–17.16
See application file for complete search history.

(56) References Cited

U.S. PATENT DOCUMENTS

| | | | | |
|---|---|---|---|---|
| 5,989,291 A * | 11/1999 | Ralph et al. | | 623/17.15 |
| 6,179,874 B1 | 1/2001 | Cauthen | | |
| 6,478,822 B1 * | 11/2002 | Leroux et al. | | 623/17.14 |
| 6,488,710 B2 * | 12/2002 | Besselink | | 623/17.15 |
| 6,592,625 B2 * | 7/2003 | Cauthen | | 623/17.16 |
| 6,613,089 B1 | 9/2003 | Estes et al. | | |
| 6,723,128 B2 * | 4/2004 | Uk | | 623/17.15 |
| 6,743,257 B2 | 6/2004 | Castro | | |
| 7,585,316 B2 | 9/2009 | Trieu | | |
| 2005/0125063 A1 * | 6/2005 | Matge et al. | | 623/17.13 |
| 2006/0265068 A1 * | 11/2006 | Schwab | | 623/17.11 |
| 2006/0282165 A1 * | 12/2006 | Pisharodi | | 623/17.12 |
| 2007/0233261 A1 | 10/2007 | Lopez et al. | | |
| 2007/0299521 A1 * | 12/2007 | Glenn et al. | | 623/17.11 |
| 2009/0112326 A1 | 4/2009 | Lehuec et al. | | |

FOREIGN PATENT DOCUMENTS

| | | |
|---|---|---|
| CN | 2899739 | 5/2007 |
| CN | 1997320 | 7/2007 |
| EP | 0716841 A1 | 6/1996 |
| EP | 1872731 A1 | 1/2008 |
| FR | 2812806 A1 | 2/2002 |
| FR | 2860428 A1 | 4/2005 |
| WO | 01/62190 A1 | 8/2001 |
| WO | 01/93786 A2 | 12/2001 |
| WO | 03/077806 A1 | 9/2003 |

(Continued)

*Primary Examiner* — Eduardo C Robert
*Assistant Examiner* — Julianna N Harvey
(74) *Attorney, Agent, or Firm* — Simpson & Simpson, PLLC (57) ABSTRACT

An artificial intervertebral spacer comprises a first arm and a second arm, each of the arms having first and second ends and wherein the first ends of each of the arms are connected together and wherein the second ends of each of the arms are generally separated from each other and divergently extend in a common direction. In a preferred embodiment, the first ends of the arms are joined to form a third arm. In a further preferred embodiment, the spacer comprises a generally Y-shaped structure. In other embodiments, at least two spacers are combined to provide an intervertebral distracting device.

19 Claims, 8 Drawing Sheets

(56) References Cited

FOREIGN PATENT DOCUMENTS

| WO | 2007-075411 A2 | 7/2007 |
| WO | 2007090017 | 8/2007 |
| WO | 2008/043906 A2 | 4/2008 |
| WO | 2008123879 | 10/2008 |

* cited by examiner

ARTIFICIAL INTERVERTEBRAL SPACER

CROSS REFERENCE TO PRIOR APPLICATIONS

This application is filed under 35 U.S.C. §120 and §365(c) as a continuation of International Patent Application PCT/CA2009/000477, filed Apr. 22, 2009, which application claims priority from U.S. Patent Application No. 61/125,094, filed Apr. 22, 2008, which applications are incorporated herein by reference in their entireties.

FIELD OF THE INVENTION

The present invention relates to the field of spinal implants and, more particularly, to implants for providing intervertebral distraction and dynamic spinal stabilization. The invention also provides the desired amount of distraction between adjacent vertebral bodies while allowing compressive forces to be absorbed.

BACKGROUND OF THE INVENTION

The spine is a complicated structure comprised of various anatomical components, which, while being flexible, provides structure and stability for the body. The spine is made up of vertebrae, each having a vertebral body of a generally cylindrical shape. Opposed surfaces of adjacent vertebral bodies are connected together and separated by intervertebral discs (or "discs"), comprised of a fibrocartilaginous material. The vertebral bodies are also connected to each other by a complex arrangement of ligaments acting together to limit excessive movement and to provide stability. A stable spine is important for preventing incapacitating pain, progressive deformity and neurological compromise.

The anatomy of the spine allows motion (translation and rotation in a positive and negative direction) to take place without much resistance but as the range of motion reaches physiological limits, the resistance to motion gradually increases, thereby bringing such motion to a gradual and controlled stop.

Intervertebral discs are highly functional and complex structures. They contain a hydrophilic protein substance that is able to attract water thereby increasing its volume. The protein, also called the nucleus pulposis, is surrounded and contained by a ligamentous structure called the annulus fibrosis (or "annulus"). The discs perform a load or weight bearing function, wherein they transmit loads from one vertebral body to the next while providing a cushion between adjacent bodies. The discs also allow movement to occur between adjacent vertebral bodies but within a limited range. In this way, the mobility (i.e., range of motion) of the spine is dependent upon the stiffness of the discs in a given segment (e.g., a pair of adjacent vertebrae) of the spine. As will be understood, such stiffness would vary depending upon the location of the spinal segment along the length of the spine. For example, a segment located in the cervical region of the spine may have a lower stiffness (i.e., greater range of motion) as compared to a segment located in the thoracic region. It will also be understood that the relative degrees of stiffness of segments would vary from one individual to another depending upon various factors that may affect the physical limits of each segment.

As will be understood, a certain amount of stiffness in spinal segments is needed for normal or symptom-free functioning. The amount of stiffness in a spinal segment can be defined as the ratio of an applied load to the induced displacement with translation or rotation. A loss of stiffness results in exaggerated movement of the associated spinal segment such as, for example, when torque is applied. From a biomechanical perspective, loss of stiffness indicates spinal instability. Exaggerated motion caused by instability or loss of physiological stiffness may result in greater stress in adjacent innervated connective tissue, and may also lead to a greater risk of nerve-root compression and irritation in the foramina.

A normally functioning intervertebral disc has the capacity to store, absorb and transmit energy applied to it. The fluid nature of the nucleus enables it to translate vertically applied pressure (axial loading) into circumferential tension in the annulus. Due to a number of factors such as age, injury, disease, etc., intervertebral discs may lose their dimensional stability and collapse, shrink, become displaced, or otherwise damaged. It is common for diseased or damaged discs to be replaced with prosthetics, or implants. One of the known methods involves replacement of a damaged disc with a spacer, which is implanted into the space originally occupied by the disc (the disc space). However, although such spacers provide the required distraction between adjacent vertebrae, they also result in or require fusion of the vertebrae. This results in essentially a solid segment and preventing any relational movement between the vertebrae within the segment. Thus, the mobility of the spinal segment is lost and additional stresses are placed on neighboring spinal segments.

Motion segment stiffness depends on the presence of a distracting force, or a force that attempts to produce positive Y-axis translation. This constant distracting force keeps not only the annular ligaments surrounding the disc space taut but also other ligaments located anteriorly and posteriorly in the spine. The motion segment then functions in a stiffer and more stable manner whereby excessive motion causing instability, pain, and neurological symptoms are reduced or eliminated. The cushioning and balancing of loads applied to the disc space are also important in attempting to restore and preserve normal functionality of the spine. Forces normally applied to the disc primarily occur from vertical loading (compression) or, in biomechanical terms, negative Y-axis translation. A device that has the inherent ability to resist or cushion negative Y-axis translation will be able to preserve disc height. However, a device that has the inherent ability to generate positive Y-axis translation (distraction) would not only be able to resist axial or Y-axis compression but would also be able to dynamically balance these loading forces acting on the disc space. Therefore, such a device would not only provide cushioning but also elastic support and balance, thereby restoring normal physiological disc function and mechanics.

Disc replacement implants that allow some movement between adjacent vertebrae have been proposed. An example of such an implant is taught in U.S. Pat. No. 6,179,874. Unfortunately, the disc replacement (i.e., implant) solutions taught in the prior art are generally deficient in that they do not take into consideration the unique physiological function of the spine. First, many of the known artificial disc implants of the prior art mainly focus on the preservation of motion without adequately addressing the restoration of normal spinal stiffness. Second, many of the known artificial disc implants are unconstrained with respect to the normal physiological range of motion in the majority of motion planes through which they move. These implants rely on existing, but in many cases diseased structures, such as degenerated facets, to limit excessive motion. This often leads to early facet joint degeneration and other collateral damage to spinal components.

The prior art also provides some intervertebral spacers that attempt to mimic the natural mobility of a spinal segment.

Examples of such spacers are provided in U.S. Pat. Nos. 5,989,291 and 6,743,257, and United States Patent Application Publication No. 2005/0125063. The '291 patent teaches a spacer formed by a pair of adjacently implanted spacer devices. Each of the devices includes opposed plates separated by at least one "Belleville washer". Although allowing for some absorption of compressive forces, the spacer of the '291 patent does not adequately allow for motion of the segment in different axes. The '257 patent teaches a generally "U" shaped spacer having a plurality of upper and lower arms protruding joined together at a fulcrum point forming the base of the "U". The '063 publication similarly teaches a "U" shaped structure. The arms are provided with bone anchoring devices and the implant is driven into the adjacent bone structures following discectomy. The device, once implanted, allows for flexing motions in the lateral and sagittal planes. However, although being adjustable to provide a specific disc height (i.e., a desired spacing between adjacent vertebral bodies), the device does not adequately allow compressive forces to be absorbed.

Thus, there exists a need for an intervertebral implant that overcomes the deficiencies of prior art solutions. More particularly, there exists a need for a spinal implant that is able to balance the reconstruction of spinal structures by restoring motion segment stiffness while at the same time allowing for the preservation of motion, particularly translation motion along the Y (or vertical) axis.

BRIEF SUMMARY OF THE INVENTION

In one aspect, the present invention provides an implant for replacing intervertebral discs. Such replacement may be made with or without a vertebral body.

In another aspect, the invention provides an artificial intervertebral implant that provides physiological stiffness to the spinal segment where it is implanted while still permitting adjacent vertebrae a range of motion about various axes. Such motion is controlled or constrained by the stiffness generated by the implant so that movement of adjacent vertebrae does not lead to deterioration of neighbouring spinal structural components.

In one aspect, the invention provides an artificial intervertebral spacer comprising first and second arms, each having first and second ends. The first and second arms are adapted for biasing apart adjacent vertebrae when the spacer in use. The first ends of each of the arms are connected together. The second ends of each of the arms extend divergently in a common direction and are generally separated from each other.

In another aspect, the invention provides an artificial intervertebral spacer comprising first and second arms, each having first and second ends. The first and second arms are adapted for biasing apart adjacent vertebrae when the spacer in use. The first ends of each of the arms are joined together along a length thereof to form a third arm. The second ends of each of the arms extend divergently in a common direction and are generally separated from each other.

In another aspect, at least one of the first and second arms is provided with an end plate for positioning against the end plate of an adjacent vertebral body when the implant is inserted into a spine. In another aspect, the end plate and the respective first or second arm are capable of articulation there-between.

In another aspect, the invention provides an intervertebral distracting device comprising two or more of the spacers of the invention.

BRIEF DESCRIPTION OF THE DRAWINGS

The nature and mode of operation of the present invention will now be more fully described in the following detailed description of the invention in view of the accompanying drawing figures, in which.

DETAILED DESCRIPTION OF THE INVENTION

At the outset, it should be appreciated that like drawing numbers on different drawing views identify identical, or functionally similar, structural elements of the invention. It also should be appreciated that figure proportions and angles are not always to scale in order to clearly portray the attributes of the present invention.

While the present invention is described with respect to what is presently considered to be the preferred aspects, it is to be understood that the invention as claimed is not limited to the disclosed aspects. The present invention is intended to include various modifications and equivalent arrangements within the spirit and scope of the appended claims.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

In the following description, the terms "superior", "inferior", "anterior", "posterior" and "lateral" will be used. These terms are meant to describe the orientation of the implants of the invention when positioned in the spine and are not intended to limit the scope of the invention in any way. Thus, "superior" refers to a top portion and "posterior" refers to that portion of the implant (or other spinal components) facing the rear of the patient's body when the spine is in the upright position. Similarly, the term "inferior" will be used to refer to the bottom portions of the implant while "anterior" will be used to refer to those portions that face the front of the patient's body when the spine is in the upright position. With respect to views shown in the accompanying figures, the term "coronal" will be understood to indicate a plane extending between lateral ends thereby separating the body into anterior and posterior portions. Similarly, the term "laterally" will be understood to mean a position parallel to a coronal plane. The term "sagittal" will be understood to indicate a plane extending anteroposterior thereby separating the body into lateral portions. The term "axial" will be understood to indicate a plane separating the body into superior and inferior portions. It will be appreciated that these positional and orientation terms are not intended to limit the invention to any particular orientation but are used to facilitate the following description.

In addition, the term "vertical" is used herein to refer to the "Y", or longitudinal axis of the spine. It will be understood that the longitudinal axis may be referred to generally as "vertical" in the context where the individual is upright. It will also be appreciated that the spine is normally not linear and that a number of curved regions exist. As such, the term "vertical" will be understood to mean a relative orientation of structures in a spinal segment and is not intended to mean orientation with respect to an external reference point. Although any methods, devices or materials similar or equivalent to those described herein can be used in the practice or testing of the invention, the preferred methods, devices, and materials are now described.

Figure 1:
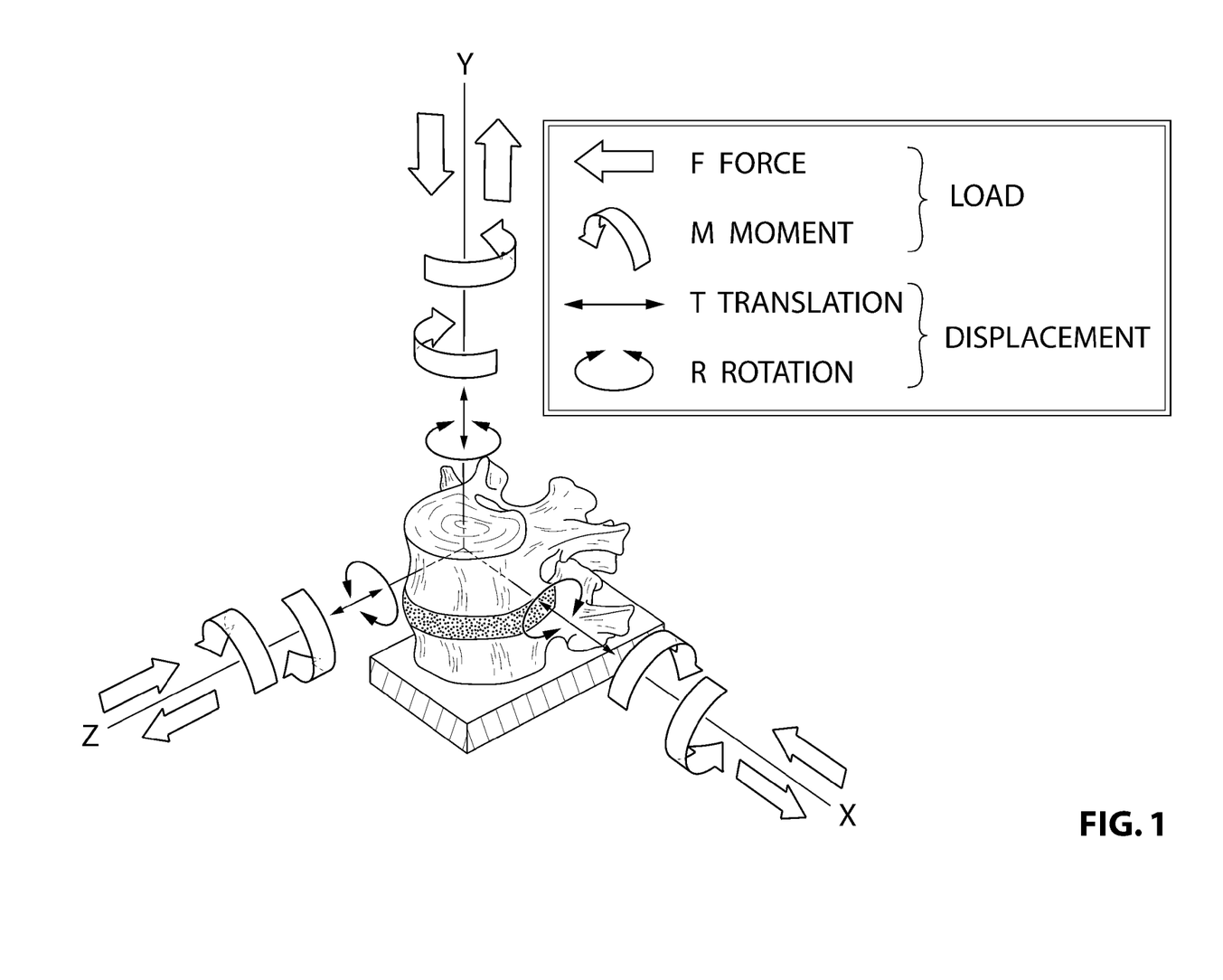
FIG. 1 is a schematic illustration of the range of motion of a vertebra.

FIG. 1 illustrates the complexity of vertebral movement by indicating the various degrees of freedom associated with a spine. In the normal range of physiological motion, vertebrae extend between a "neutral zone" and an "elastic zone". The neutral zone is a zone within the total range of motion where ligaments supporting the spinal bony structures are relatively non-stressed; that is, the ligaments offer relatively little resistance to movement. The elastic zone is encountered when the movement occurs at or near the limit of the range of motion. In this zone, the visco-elastic nature of the ligaments begins to provide resistance to the motion thereby limiting same. The majority of "everyday" or typical movements occurs within the neutral zone and only occasionally continues into the elastic zone. Motion contained within the neutral zone does not stress soft tissue structures, whereas motion into the elastic zone will cause various degrees of elastic responses. Therefore, a goal in the field of spinal prosthetic implants in particular, is to provide a prosthesis that restricts motion of the vertebrae adjacent thereto to the neutral zone. Such restriction minimizes stresses to adjacent osseous and soft tissue structures. For example, such limitation of movement will reduce facet joint degeneration.

The present invention provides implants for replacing intervertebral discs that are damaged or otherwise dysfunctional. The implant of the present invention is primarily designed to restore segmental stiffness but also to preserve motion between adjacent vertebral bodies. In general, the present invention provides spinal implants for replacing multiple intervertebral discs. In some cases, the implant of the invention may also serve to replace both a disc and one or both adjacent vertebral bodies. The implant of the invention can also be used with artificial vertebral bodies.

Figure 2:
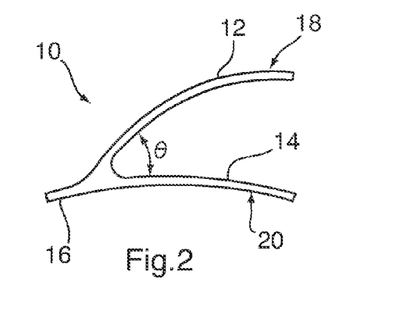
FIG. 2 is a side elevation of an implant according to one embodiment of the invention.

In one embodiment, as illustrated in FIG. 2, the invention comprises intervertebral implant 10 having a generally "Y" shaped structure in a side view, or, alternatively a generally "V" shaped structure with a tail. The implant includes a pair of diverging arms comprising first arm 12 and second arm 14 forming the diverging arms of the "V" structure of the implant. First ends of arms 12, 14 divergently extend in a common direction, while the opposite second ends of the arms are joined to each other to form a third arm or tail 16, to thereby result in the aforementioned "Y" structure. In general, when positioned in a spine, implant 10 is oriented with first arm 12 forming the superior portion of the implant and second arm 14 forming the inferior portion. As such, the arms may also be referred to as superior arm 12 and inferior arm 14. This terminology will be used for the purposes of the present description.

Utilizing a Y-shape as the basis for the implant structure is believed to have various biomechanical advantages. Tail portion 16 of implant 10 allows the above-mentioned compressive loads to be evenly distributed along its length thereby avoiding such load to be focused at a single inflection point. Such a feature of the Y-shape is exploited in the structure of the present invention. For example, the Y-shape specifically allows the function of a normal disc to be mechanically mimicked thereby restoring motion segment stiffness. Because of the diverging configuration of arms 12, 14 forming the Y-shape, a force attempting to compress the distal ends of the arms (that is, the ends opposite to tail 16) will be met with a spring-like resistance. As will be understood by persons skilled in the art, as the amount of compressive force on implant 10 increases, the distal ends of arms 12, 14 are displaced towards each other and the resistance to such displacement gradually increases due to the tensile strength of the material forming the implant and the elasticity offered by the Y-shaped structure. In other words, implant 10 functions as a spring and would have an inherent tendency to return to its uncompressed state. Further, in such uncompressed state, implant 10 would have the capability of being compressed upon application of a sufficient load. These and other characteristics, as discussed further below, therefore allow the implant to provide the required distraction of adjacent vertebrae, stiffness during movement of the respective spinal segment and absorption of compressive forces.

Various other features are realized by using the "Y" shaped structure of the present invention. First, as compared to a "U" shaped structure as known in the art, the present "Y" or "V" with a tail structure provides improved biasing functionality when positioned between adjacent vertebral bodies. Specifically, as will be understood by persons skilled in the art, the maximum separating deflection that can be achieved by a "U" shaped structure is the point at which the arms return to their original parallel arrangement. However, the generally "V" shaped structure achieved by the arms of the present invention allows greater diverging forces to be applied upon implantation. Thus, the implant of the present invention with diverging arms, as in a "V" or "Y" arrangement, has the inherent ability to continually generate a separating force within the intervertebral space. Therefore, the implant of the invention is not only able to absorb a compressive vertical force, it is also capable of more effectively generating a continual separating force against the adjacent vertebral bodies, particular during movement of the spine. It will be understood that the implant of the invention may be constructed without tail portion 16, thereby rendering generally "V" shaped structure. In other words, the tail portion of the invention may be omitted.

However, tail segment or portion 16 of the "Y" shaped implant of the invention also provides added benefits. For example, the tail segment increases the surface area of the inferior portion of the implant to maximize the surface area of the implant in contact with the superior endplate of the inferior vertebral body, when the implant is positioned in the intervertebral space. This provides for increased stability after initial placement of the implant, before osseous integration has taken place. As will be understood, by increasing the surface area in contact between the implant and the inferior vertebral body allows improved osseous integration in the long term. The larger the contact surface area, the less likely it is for the implant to subside.

Tail segment 16 of the "Y" shaped implant of the invention also facilitates the optimal positioning of the center of rotation of the implant for an individual patient. For example, if a short tail is provided, the implant can be placed deeper into the disc space, and therefore, the center of rotation created by the implant will be more posterior. Similarly, an implant with a longer tail will be associated with relatively shorter arms (of the remaining "V" shaped portion), and therefore, such implant will have a more anteriorly positioned center of rotation. As will be understood, the desired center of rotation can therefore be tailored by adjusting the proportional lengths of the arms and tail. It should be pointed out that with a "U" shaped structure, such adjustment in center of rotation can only be derived by moving the implant itself to a desired location. With the present invention, at least the inferior surface area can remain constant and the center of rotation can be adjusted simply be designing the implant to have a shorter or longer tail portion as desired. Although the above discussion has focused on the length of tail 16, it will be understood that another manner of describing this functionality would be to indicate that the junction of superior arm 12 and inferior arms 14 is positioned at a desired location along the length of the implant.

The tail segment of the implant also allows for the adjustment or optimization of the amount or degree of lordosis that is provided in the spine after insertion of the implant. As with the above description with respect to the center of rotation, short tail 16 will provide a greater separating force at the posterior portion of intervertebral space, thus resulting in less lordosis after implantation. However, as will be understood, an implant with longer tail 16 will have shorter arms 12, 14, which would therefore be of increased stiffness. This form of the implant will position the diverging ends of the legs more anterior and will therefore generate a greater separating force in the anterior intervertebral space as compared to the posterior space. As such, this form of the implant will increase lordosis of the spine when the implant is in place.

Tail 16 also facilitates the insertion of the implant into "tight" disc spaces since the implant, whose tail portion would generally have a thickness of a few millimeters, can be inserted as a wedge.

In addition, tail portion 16 also allows the implant to be positioned "backwards" into the intervertebral disc space. That is, the implant of the invention can be inserted with the ends of the arms 12, 14 instead of tail 16. In such case, tail 16 can be used to affix the device to the endplate of the adjacent vertebral body by using oblique screws. As will be understood, with the implant arranged in such "backwards" manner, the above-described issues of positioning the center of rotation and providing the desired degree of lordosis would still apply, although in reverse.

In use, implant 10 is first compressed and then inserted into the disc space between the adjacent vertebral bodies. In one embodiment, implant 10 is designed to be positioned against the endplates of the adjacent endplates of the superior and inferior vertebral bodies. However, as discussed further below, the implant of the invention may also include or be used with one or more artificial endplates or other prosthetic devices. Once positioned within the disc space, the compressive force on implant 10 is released and the device is allowed to open and bear against the adjacent vertebral bodies within the disc space. The degree to which implant 10 is allowed to open will be limited by the height of the disc space and by the tension offered by the surrounding ligaments. Continuous and dynamic Y-axis (or vertical) distraction of the spinal segment is generated by implant 10 due to the elastic force generated by the arms, which forces the arms away from each other, thereby applying a separating force against the adjacent vertebrae. As will be understood by persons skilled in the art, implant 10 may be positioned with the open end (i.e., the end opposite tail 16) being directed either anteriorly or posteriorly. As discussed further below, such positioning may also serve to provide the spinal segment with a desired degree of curvature in either the anterior or posterior directions thereby allowing the segment to assume a lordotic or kyphotic shape as needed.

It will be understood that implant 10 shown in the figures is merely representative of one embodiment. The implant can be provided in any size and, as discussed below, various shapes and configurations. It will also be understood that the size and/or thickness of arms 12, 14 or sections thereof may be adjusted in order to provide a required stiffness or distractive force. Such modifications will be within the scope of knowledge of persons skilled in the relevant art.

The compressibility and the response to compression of the Y-shape of the implant provide the ability to dynamically respond to loading forces applied thereto. The dynamic response of the device or implant can also be altered by altering the basic Y-shaped structure of the implant. For example, and as discussed further below, one or more of the implants may be combined together; the implant may be combined with existing arthroplasty devices; or the implant may be combined with another such artificial or natural component. It will also be understood that one or more of the above modifications may be used in conjunction.

Referring again to FIG. 2, each of arms 12, 14 may be divided into three segments: a proximal segment (i.e., proximal to tail 16); a middle segment; and, a distal segment (i.e., opposite tail 16). Superior arm 12 is preferably provided with convex superior surface 18 while inferior arm 14 is preferably provided with concave inferior surface 20. This preferred structure of arms 12, 14 allows implant 10 to assume a shape that is complementary to the adjacent superior and inferior vertebral bodies. It will be understood that arms 12, 14 may be provided with any variety of shapes as needed. In one embodiment, angle θ, as shown in FIG. 2, between superior arm 12 and inferior arm 14, may be between 30 to 60 degrees. However, various other values for this angle may be possible.

FIGS. 22*a* to 22*d* illustrate various views of the implant of FIG. 2.

Due to the structure of arms 12, 14 discussed above and shown in the figures, it will be understood that superior arm 12 would function in a "spring board" like fashion. As such, superior arm 12 may be primarily responsible for the functioning of the device, with inferior arm 14 and tail 16 serving more of a stabilizing function.

As will be understood, in order to provide the functional characteristics as herein described, implant 10 is generally formed of a resilient material that allows the implant to provide the required distracting force to keep adjacent vertebrae separated by the desired distance while also allowing a desired amount of compression. Once the compressive force on implant 10 is removed, the device is designed to return to its non-compressed shape, while still restricted within the disc space. The various portions of implant 10 can be manufactured from the same or different materials. Therefore, each section of the implant can be provided with the same or different elastic properties depending on the need. For example, as described above, superior arm 12 may, in one embodiment, be manufactured from a material that is more elastic than inferior arm 14. The implant may be made from various known materials known in the art such as, for example, carbon fiber, simple or advanced plastics such as polyether-etherketone (PEEK), shape metal alloys such as Nitinol™ or more commonly used materials such as cobalt chrome, stainless steel or titanium alloys. In general, implant 10 is formed from one or more materials having a tensile strength sufficient to provide an elastic force allowing the implant to have a spring-like functionality.

In one embodiment, desired external surfaces of implant 10 may be provided with a surface structure or coating to promote bone in-growth, and thereby, allow anchoring of the implant in the disc space. In a preferred embodiment, the inferior surface of the implant, i.e., inferior surface 20 of inferior arm 14 and the inferior surface of tail 16, are generally optimized for bone in-growth, thereby providing for the main means of initial fixation and long-term stability of the device. These surfaces of the implant could be prepared through commercially available means including plasma spray and hydroxyapatite coating, etc. Initial fixation could be achieved through screw fixation through the superior surface of inferior arm 14 into the inferior endplate (not shown) of the disc space. Fixation could also be achieved using spikes on inferior surface 20 of inferior arm 14. Various other means of fixation of the implant will be known to persons skilled in the art and will be applicable with the present invention. Further, in a preferred embodiment, the superior surface may be treated to prevent bone in-growth. Such an arrangement will result in a resurfacing effect wherein the cartilaginous and bony inferior endplate of the superior vertebra articulates directly with the implant.

As will be understood by persons skilled in the art having regard to the present description, the implant of the invention can be modified in a number of ways. For example, arms 12, 14 and tail segment 16 may be adjusted in length or in thickness. Further, such modifications in length and thickness may be made either for the enter length of these implant sections or along a portion thereof In addition, the geometry of the angles provided on the implant may also be increased or decreased. These modifications taken individually or in a combination will allow for a variety of stiffness characteristics to be provided for the implant. For example, shortening the superior arm will result in increased stiffness while lengthening would decrease stiffness. Similarly, thickening of the superior arm will provide increased stiffness as compared to a relatively thinner arm. It will be understood that a variety of stiffness characteristics may be required along the spine of a single individual. That is, the motion requirements and restrictions of vertebral segments along the spine will vary from one segment to the next. For example, the motion and forces within a cervical spinal segment may be considerably different from those of a lumbar segment. As such, the ability of the implant to be modified in numerous ways provides a unique advantage in that it may be used in various spinal locations.

In addition to the above-mentioned modifications to the implant, the superior and/or inferior arms may also be modified by tapering its thickness thereby allowing a gradual change in stiffness characteristics to be provided along their length. It will be understood that the advantage offered by this and other modifications may be more effectively realized in superior arm 12.

Figure 3:
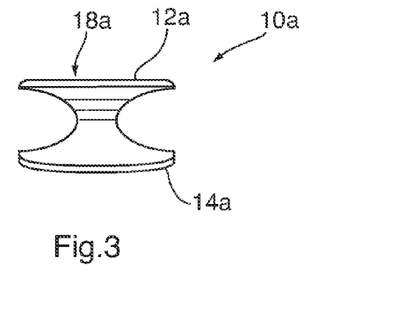
FIG. 3 is an end elevation of an implant according to another embodiment of the invention.
Figure 4:
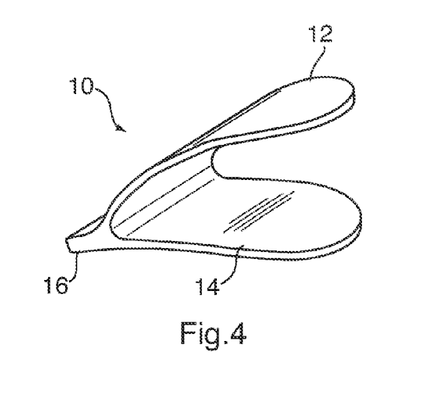
FIG. 4 is a side perspective view of an implant according to another embodiment of the invention.

As a further modification, arm 12 and/or arm 14 and tail 16 may also vary in width along their length. For example, FIG. 4 illustrates implant 10 having superior arm 12 and inferior arms 14, wherein their widths are essentially constant along their lengths. FIG. 3 illustrates another embodiment of the invention wherein implant 10a includes superior arm 12a and inferior arm 14a, wherein the widths of the arms are gradually reduced from the distal to the proximal ends (i.e., in a direction towards tail 16). As will be understood, having a wider superior arm (such as shown in FIG. 4) will provide a stiffer device than having a narrow or narrowing superior arm (such as shown in FIG. 3) for the same thickness.

In a further advantage of the invention, by tapering the width of one or both of arms 12, 14 and/or tail 16, the implant may be allowed to move in other planes. For example, as shown in FIG. 3, by tapering, in particular, the width of superior arm 12a towards its proximal end (the end proximal to tail 16), superior arm 12a is rendered able to move in additional planes. In this way, implant 10a allows for additional degrees of movement of the spinal segment such as to allow lateral flexion, or rotation. In biomechanical terms, the segment is provided with a certain degree of freedom relating to movement in the Z-axis and rotation about the Y-axis. Again, it will be understood that such tapering in width of arm 12a may be accompanied by one or more of the other modifications discussed herein such as, inter alia, choice of material, thickness and length.

Figure 5:
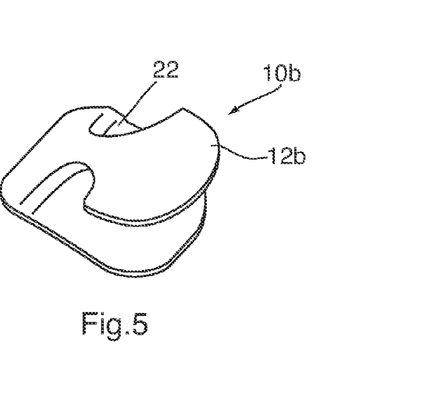
FIG. 5 is a top perspective view of an implant according to another embodiment of the invention.

In a further modification, the width of the superior arm is shown in FIG. 5 wherein superior arm 12b of implant 10b is provided with discrete section 22 of reduced width. As with the embodiment shown in FIG. 3, superior arm 12b of FIG. 5, having reduced width section 22, or a "waist", allows implant 10b to move in additional planes, and thereby, allows the spinal segment, when the implant is in place, a greater range of motion.

In the above discussion, reference has been made to providing desired degrees and ranges of motion by physically modifying the implant of the invention. However, it should also be pointed out that positioning of the device may also allow for various modifications to be realized. For example, the nature of the implant, that is, by having a pair of articulating arms joined at a common section, provides the ability to concentrate the force by the implant in the area of the adjacent vertebral structures contacting the implant surfaces. For example, if the distal end of the superior arm is positioned under the antero-inferior aspect of the superior vertebral body, most of the lifting or distracting force provided by the implant will be focused in such anterior region as opposed to the posterior region of the adjacent vertebra. This will therefore lead to more distraction of the disc space anteriorly rather than posteriorly, thereby allowing for restoration or reconstruction of lordosis.

Figure 6:
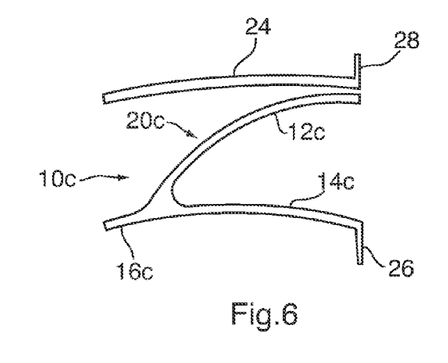
FIGS. 6 to 9 are side elevations of implants according to another embodiment of the invention wherein a superior end-plate is provided.
Figure 7:
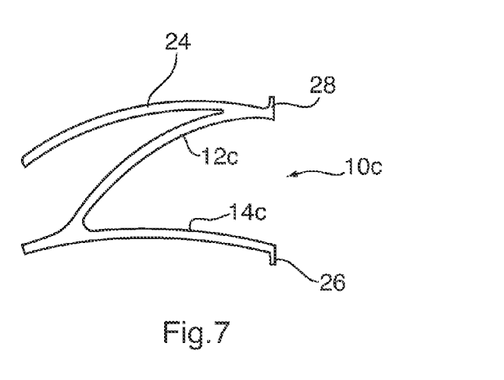
Figure 8:
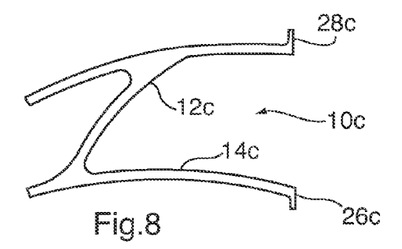
Figure 9:
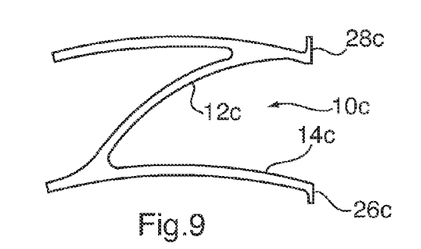

In addition to modifying the physical structure of the implant of the invention, various other additional features may be provided. For example, as shown in FIGS. 6 to 9, superior arm 12c of implant 10c may be provided or associated with artificial endplate 24, which is designed or adapted to be affixed to the inferior surface of the superior vertebral body once implant 10c is in place within the disc space. As shown in FIGS. 6 to 9, endplate 24 may be provided in a variety of ways. For example, as shown in FIG. 6, the endplate may be provided as a separate element to engage superior surface 20c of superior arm 12c. Alternatively, as shown in FIGS. 7 to 9, endplate 24 may be secured to superior arm 12c or may be formed as an integral unit with same. As further illustrated in FIGS. 7 and 8, superior arm 12c may be designed to allow endplate 24 to be connected to or contact superior arm 12c in a variety of sections. For example, FIG. 7 illustrates endplate 24 connected to the distal end or tip of superior arm 12c whereas in the embodiment illustrated in FIG. 8, endplate 24 is connected to a middle region of superior arm 12c. As discussed above, by varying the contact position between endplate 24 and superior arm 12c, a variety of stiffness characteristics and intervertebral positioning characteristics may be provided depending upon the need. Another variant of the endplate arrangement can be seen by comparing FIGS. 7 and 9. Specifically, endplate 24 may be connected to superior arm 12c such that endplate 24 is generally parallel to inferior arm 14c (as shown in FIG. 9) or such that endplate 24 is angled with respect to inferior arm 14c (as shown in FIG. 7). By providing endplate 24 in a parallel orientation with respect to inferior arm 14c and connected to the middle of superior arm 12c, the resulting distractive force will be applied parallel to the middle of the disc space thereby resulting in symmetrical distraction. Similarly, when superior endplate 24 is attached to superior arm 12c at its distal end and where the distal end of implant 10c is positioned anteriorly in the disc space, and endplate 24 is attached at an angle to the inferior arm (such as shown in FIG. 7), maximal lordosis will be established as the anterior disc height would be distracted more than the posterior disc height.

Referring again to the embodiment illustrated in FIG. 6, it will be appreciated that by not having superior endplate 24 secured to superior arm 12c, movements such as flexion and extension would be less restricted since endplate 24 and superior arm 12c would be in sliding contact. In such case, superior endplate 24 may be provided with ridges (not shown) on its lateral sides that could act as guides or stops for the distal edge of the superior arm so as to limit the range of flexion and extension. Such guides on endplate 24 could also allow for various degrees of rotation depending on the amount of freedom allowed between the lateral edges of superior arm 12c and the guides. This feature could, of course, be used with or without providing a waist or taper on superior arm 12c such as that shown in FIGS. 3 and 5.

Figure 19:
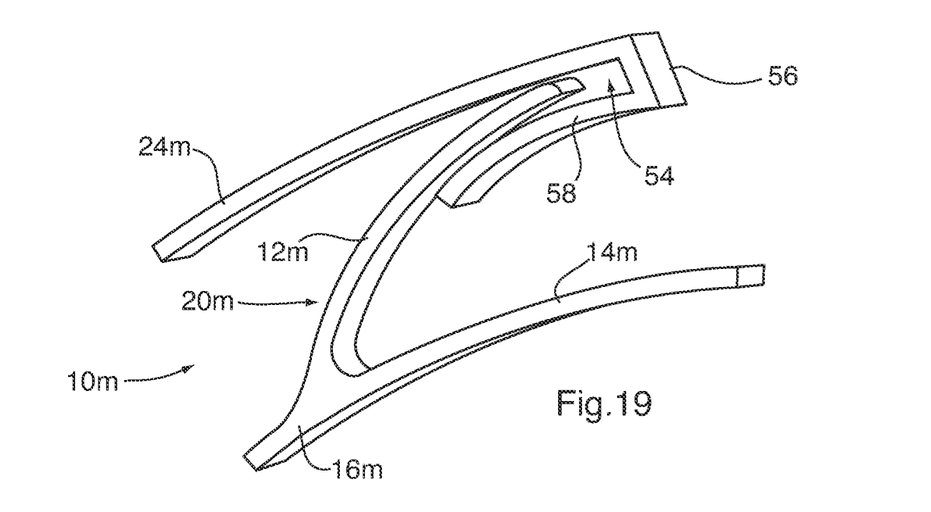
FIG. 19 is a side perspective view of a variant of the embodiment shown in FIG. 6.

In a variation of the embodiment of FIG. 6 shown in FIG. 19, like elements are identified with the same reference numerals but with the letter "m" added for clarity. As shown in FIG. 19, and similar to FIG. 6, superior arm 12m is not secured to superior endplate 24m. However, in the embodiment shown, endplate 24m includes pocket or groove 54 adapted to accommodate at least a portion of the distal end of superior arm 12m. In one aspect of the invention, pocket 54 comprised of inferiorly extending edge 56 and flange 58 extending towards tail 16m. However, it will be understood that pocket 54 can be formed in another manner while still achieving the results described herein. Pocket 54 is preferably sized to allow superior arm 12m to be moveable there-within to allow the same movement characteristics as the embodiment of FIG. 6. In this regard, flange 58 is provided with a curvature that is complementary to that of superior arm 12m. The embodiment shown in FIG. 19 would therefore serve to maintain the articulating portion of superior arm 12m covered, and thereby, serve to prevent or inhibit soft tissue ingrowth.

In the embodiments shown in FIGS. 6 to 9, superior end plate 24 may be provided with a means for fixing or fusing the endplate to the adjacent vertebral body. For example, the superior or external surface of endplate 24 may be provided with a surface texture or coating to initiate or encourage bone fusion.

FIGS. 6 to 9 also illustrate a further optional feature of the implant. Specifically, in FIGS. 6 to 9, the distal end of inferior arm 14c is shown as being provided with inferiorly extending edge 26 that serves to assist in the placement of implant 10c against the inferior vertebral body (not shown) as discussed further below. Similarly functioning edge 28, although superiorly extending, may also be provided on the distal end of endplate 24. It will also be understood that in embodiments not including endplate 24, such as shown in FIG. 2, superior arm 12 may include a similar superiorly extending edge. In operation, edges 26, 28 serve to bias the implant against the outer edges of the vertebral bodies between which it is implanted. Thus, in the typical case where the implant is surgically inserted between adjacent vertebral bodies in an anterior approach, edge 26 and/or edge 28 abut against the anterior edges of the respective vertebral bodies and prevent further insertion of the implant.

Figure 20:
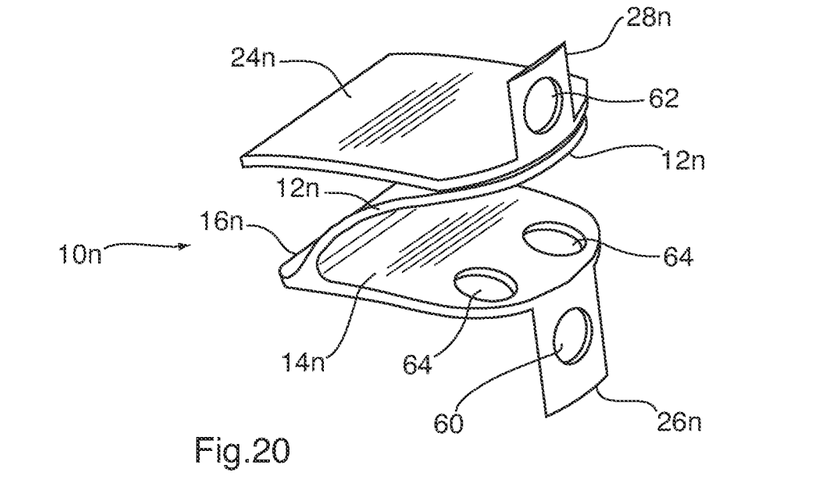
FIG. 20 is a top perspective view of a variant of the embodiment shown in FIG. 6.

FIG. 20 illustrates a further embodiment of the invention illustrating a variation in the edges discussed above. This embodiment specifically illustrates such variation with reference to the embodiment of FIG. 6. Thus, as in FIG. 6, superior arm 12n of implant 10n is not connected to superior endplate 24n and is therefore allowed to articulate with respect to the latter. Superior endplate 24n and inferior arm 14n are provided with respective edges 28n, 26n that extend oppositely as described above. Thus, edge 28n of superior endplate 24n extends superiorly with respect to implant 10n while edge 26n of inferior arm 14n extends inferiorly. As explained above, edges 26n, 28n are adapted to bear against the outer sides of the respective adjacent vertebral bodies (not shown). With the embodiment of FIG. 20, edges 26n, 28n include at least one aperture or hole 60, 62, respectively. Apertures 60, 62 are adapted to receive screws (not shown) as commonly known in the art. The screws will be adapted to be inserted through aperture 60 and/or aperature 62 and to be secured to the adjacent bone structure of the respective vertebral bodies. As will be understood, with such arrangement, superior endplate 24n and inferior arm 14n are secured to the respective vertebral bodies and prevented from moving with respect to the same. Thus, the movement of the spinal segment will therefore be restricted to articulation between superior arm 12n and superior endplate 24n. It will be understood that additional apertures or screw holes may be provided for further stabilizing portions of the implant against neighboring structures. For example, as shown in FIG. 20, inferior arm 14n may include such additional apertures 64, extending therethrough, which would also be adapted to receive bone anchoring screws. In such case, and as shown in FIG. 20, apertures 64 may need to be provided obliquely in order to accommodate angular implantation of the anchoring screws.

FIGS. 23a to 23d illustrate various views of the implant of FIG. 6. As described above, the embodiment of FIGS. 6 and 23a to 23d offers the feature of superior endplate 24 not being secure to implant 10a. This arrangement therefore allows for various degrees of articulation between superior arm 12 and superior endplate 24. In prior art devices, such as the known "U" shaped devices described above, both the superior and inferior arms of the device are taught as being secured to the adjacent vertebral bodies. As such, the present invention provides an improvement over such teaching by allowing a greater range of motion.

Figure 10:
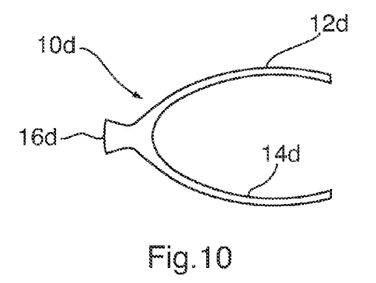
FIGS. 10 and 11 are side elevations of implants according to another embodiment of the invention, including modifications of the tail segment.
Figure 11:
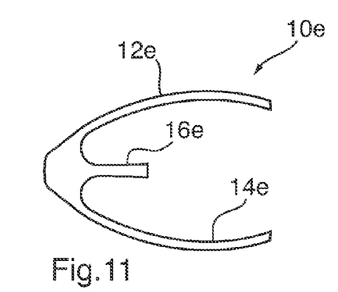

Although the aforementioned embodiments have referred to the implant of the invention as having a generally "Y"

shaped structure, modifications of this form are also contemplated within the scope of the present invention. For example, as shown in FIG. 10, implant 10d has superior arm 12d and inferior arm 14d, respectively, as before but, in this case, tail 16c is of a different shape and structure, namely, shorter in length. Alternatively, as shown in FIG. 11, implant 10e includes arms 12e, 14e as with FIG. 10 but, in this case, tail 16e is directed in the same direction as the arms. The embodiment of FIG. 11 allows implant 10e to be placed into the disc space and symmetrically distract both the superior and inferior endplates of the disc space.

FIGS. 10 and 11 also illustrate an embodiment wherein inferior arm 14d, 14e is provided with the same cross sectional configuration as superior arm 12d, 12e. As mentioned-above, such an arrangement again allows the implant to symmetrically distract the disc space in both superior and inferior directions.

Figure 12:
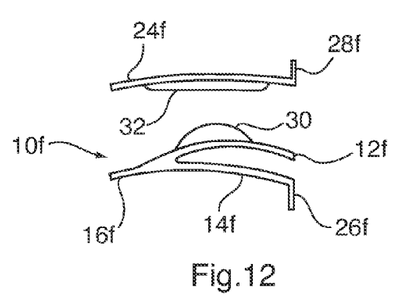
FIG. 12 is a side elevation of the invention according to another embodiment of the invention, including an articulation means.

FIG. 12 illustrates an embodiment of the invention, which allows for complex articulation of the spinal segment. In the embodiment shown, implant 10f is adapted to include a ball and socket type of design. As shown, superior surface 20f of superior arm 12f is provided with partial spherical portion 30, which forms the "ball" portion of the arrangement. "Socket" 32 is provided on the inferior surface of endplate 24f. As will be understood, endplate 24f of FIG. 12 would preferably not be fixed to superior arm 12f in a manner similar to that shown in FIG. 6. Such an arrangement therefore allows endplate 12f and superior arm 12f to move, or articulate with respect to each other. Socket 32 may be of any shape as will be known to persons skilled in the art in order to allow a range of motion of associated ball 30 but wherein such motion is restricted at outer limits to prevent dislocation. Although a ball and socket combination has been shown and described above, it will be appreciated that other types of joints may also be used. For example, in one alternative embodiment, the location of the ball and socket portions may be reversed to locate the ball portion on the inferior surface of superior endplate 24f and the socket portion on the superior surface of superior arm 12f. In other embodiments, the ball and socket may be substituted with a tongue and groove combination, which would allow a range of motion in one plane. Alternatively, the ball and socket combination may be substituted with a floating core contained within a cavity. The cavity may be formed by partial cavities being provided on the opposed surfaces of endplate 24f and the superior surface of superior arm 12f and the floating core provided there-within. Various other alternatives will be apparent to persons skilled in the art to allow a restricted range of different motion types as between endplate 24f and superior arm 12f in one or more planes.

Figure 21:
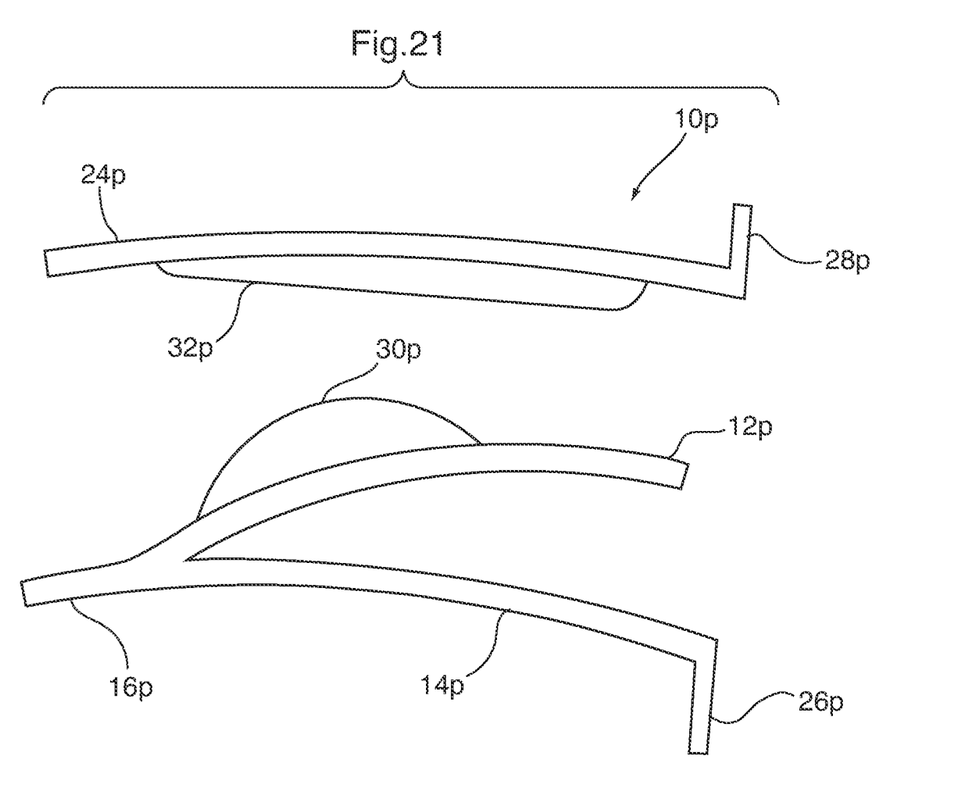
FIG. 21 is a side elevation of the embodiment shown in FIG. 12.
Figure 22A:
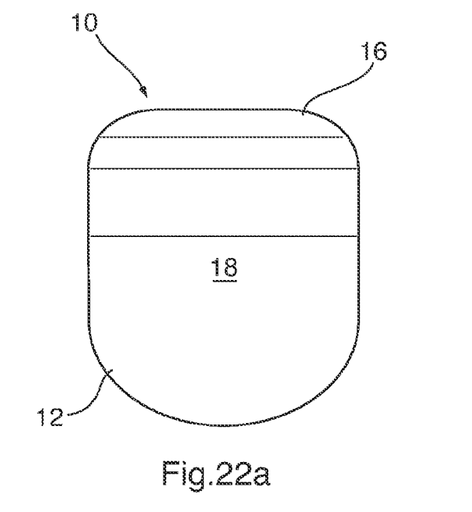
FIG. 22a is a top view of the implant of FIG. 2.
Figure 22B:
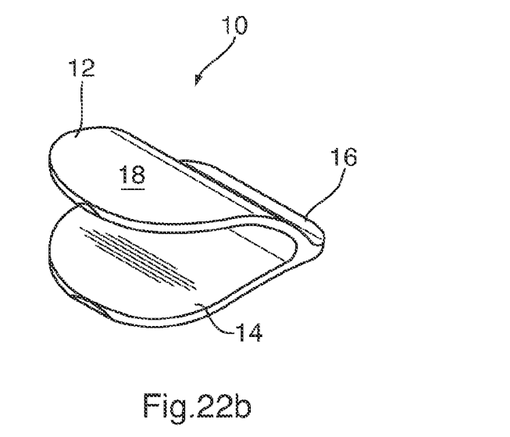
FIG. 22b is a perspective view of the implant of FIG. 2.
Figure 22C:
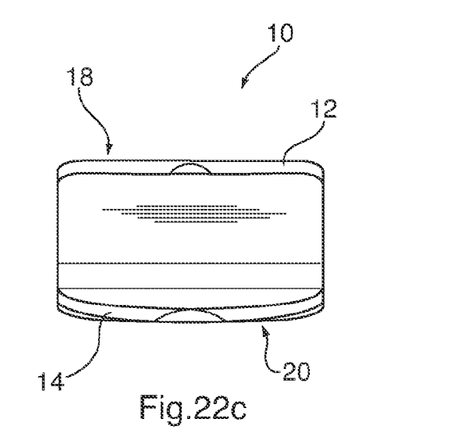
FIG. 22c is an anterior end view of the implant of FIG. 2.
Figure 22D:
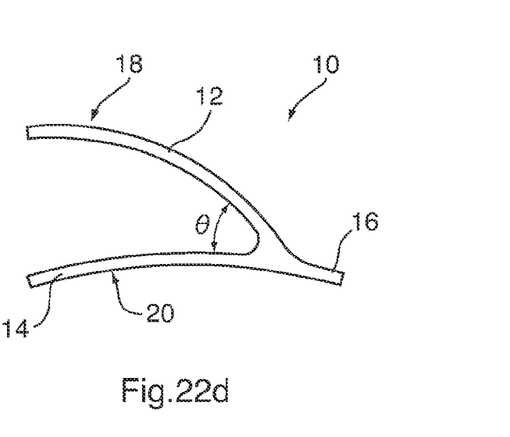
FIG. 22d is a side elevation of the implant of FIG. 2.
Figure 23A:
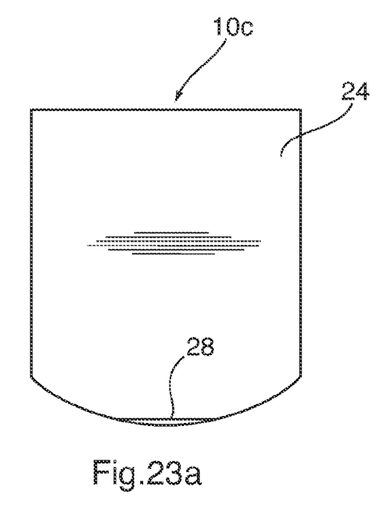
FIG. 23a is a top view of the implant of FIG. 6.
Figure 23B:
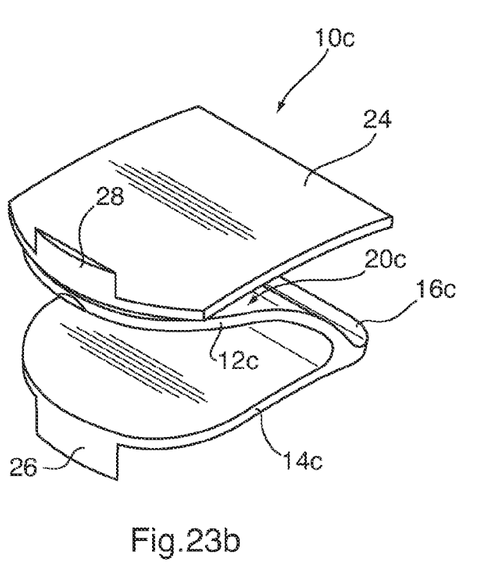
FIG. 23b is a perspective view of the implant of FIG. 6.
Figure 23C:
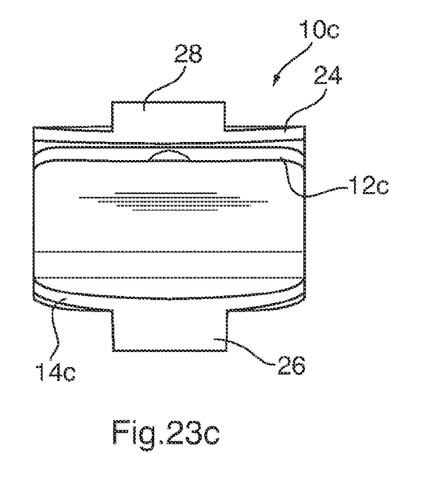
FIG. 23c is an anterior end view of the implant of FIG. 6.
Figure 23D:
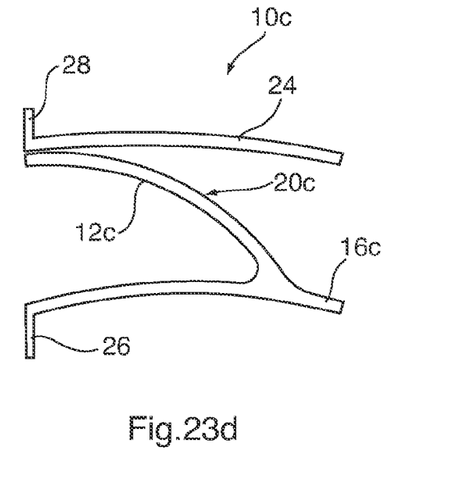
FIG. 23d is a side elevation of the implant of FIG. 6.

Although "ball" 30 of FIG. 12 is shown to be positioned at the distal end of superior arm 12f, it will be understood that such location can be at various different positions over the surface of superior arm 12f. For example, as shown in FIG. 21, where like elements are referred to with the same number but with the letter "p" added for clarity, ball 30p is located closer to the proximal end of superior arm 12p (i.e., closer to tail or third arm 16p). As will be appreciated, moving the position of ball 30, 30p, would result in a different range of articulating movement between superior arm 12, 12p and superior end plate 24, 24p. In a similar manner, the relative size and/or shape of the ball and the socket may also be varied in order to provide additional variations in articulations.

Figure 13:
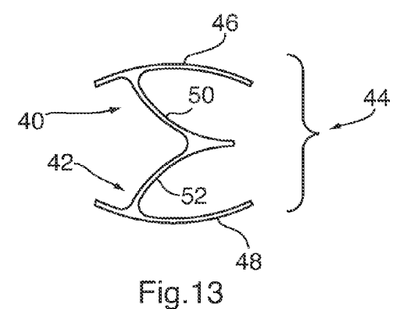
FIGS. 13, 14, and 17 are side elevations of implants according to another embodiment of the invention wherein multiple devices are used in combination.
Figures 14, 15, 16, 17, 18:
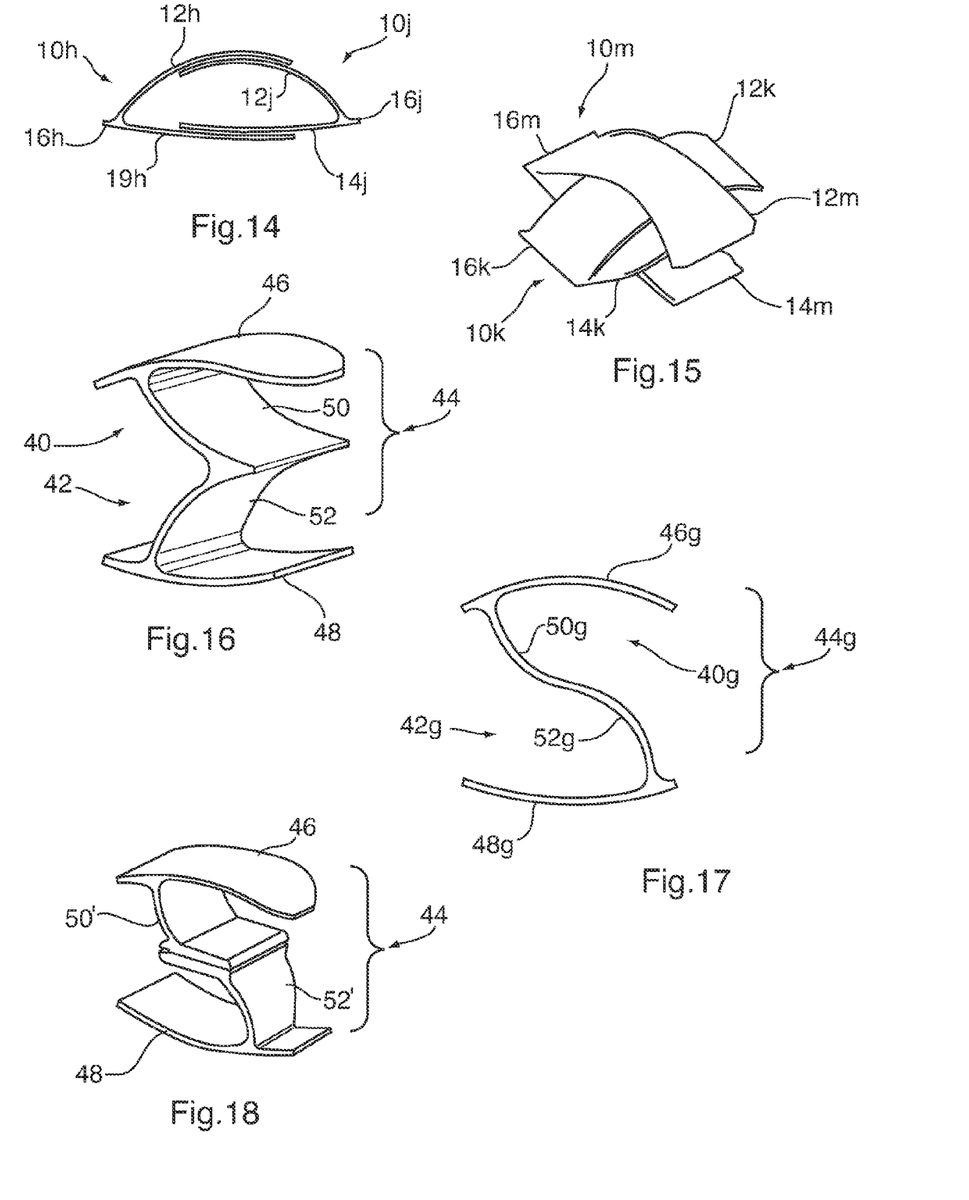
FIGS. 15, 16, and 18 are side perspective views of implants according to another embodiment of the invention wherein multiple devices are used in combination.

In another embodiment, at least two of the above described Y-shaped implants may be combined and positioned within the same disc space. For example, as shown in FIGS. 13 and 16, two Y-shaped devices 40, 42 are combined to form implant 44. The devices are arranged vertically so that first device 40 is provided superiorly while second device 42 is provided inferiorly. In such arrangement, devices 40, 42 may, as shown in FIGS. 13 and 16, be mirror images of each other. That is, superior arm 46 of superior device 40 is structurally similar in appearance to inferior arm 48 of inferior device 42. Similarly, inferior arm 50 of superior device 40 is similar in shape to superior arm 52 of inferior device 42. In the embodiment shown, inferior arm 50 and superior arm 52 of adjacent devices 40, 42, respectively, are connected or formed together. Thus, the combination of arms 50, 52 serves to function as the tail as described previously. Moreover, it will be noted that implant 44 is structurally similar to that depicted in FIG. 11. This embodiment of the invention provides implant 44 that allows for additional implant height and may be used in cases where increased height is required such as for a corpectomy. The attachment of arms 50, 52 to each other can be fixed or could allow for some relative movement therebetween.

FIG. 18 provides a further embodiment of the implant shown in FIGS. 13 and 16. In FIG. 18, implant 44 is similar to that described above with the exception that arms 50' and 52' contact each other through flattened surfaces provided thereon. In this arrangement, arms 50' and 52' are allowed to slide over each other across such flattened surfaces.

In a further variation of the implant in FIGS. 13 and 16 and illustrated in FIG. 17, implant 44g is comprised of the same superior device 40g and inferior device 42g but wherein one of such devices is rotated such that the respective arms, 46g and 50g, 52g and 48g, of each device are directed in opposite directions.

In a further embodiment of the invention illustrated in FIGS. 14 and 15, two Y-shaped implants, such as that shown in FIG. 2, are combined separately. In the embodiment shown in FIG. 14, first implant 10h and second implant 10j are provided. Each of implants 10h and 10j include superior and inferior arms (12h, 14h, 12j, 14j) as described previously. Second implant 10j is designed to allow arms 12j, 14j thereof to be inserted between the arms 12h, 14h of the first implant. In one embodiment, second implant 10j is designed to be smaller and stiffer. In this manner, second implant 10j serves to support first implant 10h and offers dynamic response to significant loads such as in the lumbar spine or thoracic spine. Although the embodiment of FIG. 14 shows two implants 10h, 10j directed in opposite directions (i.e., with the arms of each implant facing oppositely and towards tails 16h, 16j of the other implant), any other orientation may also be possible. For example, the implants may be directed orthogonally with respect to each other or in any other angular arrangement whereby the implant would assume an "X" shape.

An example of such an "X" shaped arrangement of two implants is illustrated in FIG. 15. As shown, two implants 10k, 10m are provided in an orthogonal arrangement wherein superior arm 12k and inferior arm 14k, respectively of one implant 10k are contained within superior arm 12m and inferior arm 14m, respectively, of other implant 10m. One advantage of the arrangement shown in FIG. 15 is that it can be placed percutaneously without the need for complete removal of the nucleus pulpusis.

The volume of space occupied by the implants shown in FIGS. 14 and 15 is relatively little since the implants are essentially two "hollow" devices. It is also noted that the amount of Y-axis distraction generated by combining the two implants essentially creates a vacuum effect inside the disc space (specifically within the paired devices) thereby resulting in the recreation of the disc space while providing a vacuum created gradient where disc fragments can migrate to.

In the above description of the invention, various modifications have been discussed. It will be understood that any of combination of one or more of these modifications may be used to achieve a desired result. For example, the embodiments shown in FIGS. 5 and 7 may be combined to provide an implant having a superior arm with a "waist" or a portion with a reduced width and wherein an endplate is attached. Similarly, any of the spacers shown in FIGS. 10 to 18 may be combined with one or more artificial endplates such as shown in FIGS. 6 to 9. It will be understood that by combining such modifications, the advantages from each may be realized in a single implant or distraction device.

Although the invention has been described with reference to certain specific embodiments, various modifications thereof will be apparent to those skilled in the art without departing from the purpose and scope of the invention as outlined in the claims appended hereto. Any examples provided herein are included solely for illustrating the invention and are not intended to limit the invention in any way. Any drawings provided herein are solely for illustrating various aspects of the invention and are not intended to be drawn to scale or to limit the invention in any way. The disclosures of all prior art recited herein are incorporated herein by reference in their entireties.

What is claimed is:

1. An artificial intervertebral spacer, said spacer being adapted to fit within an intervertebral space between adjacent first and second vertebral bodies, each of said first and second vertebral bodies having a superior surface and an inferior surface, the intervertebral space being bounded by the inferior surface of the first vertebral body and the superior surface of the second vertebral body, the artificial intervertebral spacer comprising:
    resilient first and second arms each having first and second ends;
    the first and second arms being adapted for elastically biasing apart said adjacent vertebral bodies when said spacer is in use, wherein the first arm is adapted to bear against the inferior surface of the first vertebral body and the second arm is adapted to bear against the superior surface of the second vertebral body;
    the first ends of each of the arms being connected together;
    the second ends of each of the arms divergently extending in a common direction and being generally separated from each other;
    wherein the first arm extends in a single direction away from the first end towards the second end thereof; and,
    the first ends of each of the arms being joined together along a length thereof to form a third arm, wherein the third arm extends in a direction opposite from the second ends of the first and second arms whereby the spacer has a generally Y-shaped structure.

2. The spacer of claim 1, wherein at least one of said first and second arms is provided with an artificial end plate for engaging an adjacent vertebral body when said spacer is in use.

3. The spacer of claim 2, wherein said end plate is connected to said at least one arm.

4. The spacer of claim 2, wherein said at least one of the first and second arms includes a first articulating surface and said end plate includes a second articulating surface, whereby said first and second articulating surfaces cooperate to allow articulation there-between when the spacer is in use.

5. The spacer of claim 4, wherein one of said first and second articulating surfaces includes a convex section and the other of said articulating surfaces includes a concave section whereby the convex and concave sections cooperate to provide a ball and socket connection when the spacer is in use.

6. The spacer of claim 1, wherein the first and second arms are generally planar.

7. The spacer of claim 1, wherein at least one of said first and second arms includes a bearing edge for bearing against an edge of one of the adjacent vertebral bodies and, thereby, for positioning said spacer, when said spacer is in use.

8. The spacer of claim 7, wherein said bearing edge includes at least one aperture for receiving a bone fastener.

9. The spacer of claim 1, wherein at least one of said first and second arms includes a waist section having a reduced width.

10. The spacer of claim 1, wherein at least one of said first and second arms includes at least one aperture for receiving a bone fastener.

11. The spacer of claim 1, wherein at least one surface of the spacer is provided with a surface structure or coating to promote bone in-growth.

12. The spacer of claim 1, wherein at least one surface of the spacer is provided with a surface structure or coating to prevent bone in-growth.

13. The spacer of claim 1, wherein the third arm is adapted to bear against the inferior surface of the first vertebral body or against the superior surface of the second vertebral body.

14. The spacer of claim 1, wherein the second end of the first arm is a free end.

15. An artificial intervertebral distracting device comprising at least two spacers according to claim 1.

16. The distracting device of claim 15, wherein two of said spacers are combined together.

17. The distracting device of claim 16, wherein one of said spacers is contained within the other.

18. The distracting device of claim 16, wherein the two spacers are oppositely directed with respect to each other.

19. The distracting device of claim 18, wherein the two spacers are in an X-shaped arrangement with respect to each other.

* * * * *